United States Patent
Castaing et al.

(10) Patent No.: US 10,334,772 B2
(45) Date of Patent: Jul. 2, 2019

(54) GROWTH ENHANCEMENT OF PLANT

(71) Applicant: RHODIA OPERATIONS, Paris (FR)

(72) Inventors: Jean-Christophe Castaing, Sevres (FR); Zhiyun Chen, Bristol, PA (US); Pengfei Ji, Shanghai (CN); Benoit Abribat, Ponthierry (FR); Galder Cristobal, Singapore (SG)

(73) Assignee: RHODIA OPERATIONS, Paris (FR)

( * ) Notice: Subject to any disclaimer, the term of this patent is extended or adjusted under 35 U.S.C. 154(b) by 0 days.

(21) Appl. No.: 14/903,241

(22) PCT Filed: Jul. 8, 2014

(86) PCT No.: PCT/CN2014/081855
§ 371 (c)(1),
(2) Date: Jan. 6, 2016

(87) PCT Pub. No.: WO2015/003624
PCT Pub. Date: Jan. 15, 2015

(65) Prior Publication Data
US 2016/0150719 A1 Jun. 2, 2016

(30) Foreign Application Priority Data
Jul. 8, 2013 (CN) .............. PCT/CN2013/078977

(51) Int. Cl.
*A01N 25/00* (2006.01)
*A01C 1/06* (2006.01)
*A01N 25/10* (2006.01)
*C08B 37/00* (2006.01)
*C09D 105/00* (2006.01)

(52) U.S. Cl.
CPC ............. *A01C 1/06* (2013.01); *A01N 25/00* (2013.01); *A01N 25/10* (2013.01); *C08B 37/009* (2013.01); *C08B 37/0087* (2013.01); *C08B 37/0096* (2013.01); *C09D 105/00* (2013.01)

(58) Field of Classification Search
CPC .......... A01N 25/10; A01N 25/00; A01C 1/06; C08B 37/0087; C08B 37/009; C08B 37/0096
See application file for complete search history.

(56) References Cited

U.S. PATENT DOCUMENTS

| | | | | |
|---|---|---|---|---|
| 4,277,364 A | * | 7/1981 | Shasha | A01N 25/28 504/250 |
| 4,780,987 A | * | 11/1988 | Nelsen | A01C 1/06 47/57.6 |
| 5,554,445 A | | 9/1996 | Struszczyk et al. | |
| 2004/0077498 A1 | | 4/2004 | Lynch | |
| 2010/0314115 A1 | * | 12/2010 | Moradi-Araghi | C09K 8/887 166/305.1 |
| 2011/0113983 A1 | * | 5/2011 | Bernu | |

FOREIGN PATENT DOCUMENTS

| | | | | |
|---|---|---|---|---|
| CN | 101999415 A | | 4/2011 | |
| WO | 9953755 A1 | | 10/1999 | |
| WO | 03094592 A2 | | 11/2003 | |
| WO | WO-3094592 A2 | * | 11/2003 | |
| WO | 2004071195 A1 | | 8/2004 | |
| WO | 2004112733 A1 | | 12/2004 | |
| WO | 2012118795 A2 | | 9/2012 | |
| WO | WO 2012/118795 | * | 9/2012 | .............. A01C 1/00 |

* cited by examiner

*Primary Examiner* — Johann R Richter
*Assistant Examiner* — Danielle Sullivan
(74) *Attorney, Agent, or Firm* — Jarrod N. Raphael

(57) ABSTRACT

Provided is a method to increase the growth of a plant by coating a seed of said plant with a composition comprising at least one of various cationic compounds; notably permitting to develop its biomass and reach its maturity. Provided also is a seed coating composition used in such a method.

18 Claims, No Drawings

GROWTH ENHANCEMENT OF PLANT

This application is a U.S. national stage entry under 35 U.S.C. § 371 of International Patent Application No. PCT/CN2014/081855, filed Jul. 8, 2014, which claims priority to International Patent Application No. PCT/CN 2013/078977, filed Jul. 8, 2013, the whole content of each of these applications is hereby incorporated herein by reference for all purposes.

The present invention concerns a method to increase the growth of a plant by coating a seed of said plant with a composition comprising at least one of various cationic compounds; notably permitting to develop its biomass and reach its maturity. The invention also concerns a seed coating composition used in such a method.

PRIOR ART

The following discussion of the prior art is provided to place the invention in an appropriate technical context and enable the advantages of it to be more fully understood. It should be appreciated, however, that any discussion of the prior art throughout the specification should not be considered as an express or implied admission that such prior art is widely known or forms part of common general knowledge in the field.

Economic demands, environmental concerns, and ecological considerations require that farmers continually improve their agricultural practices. These economic demands require that farmers utilize the most cost efficient practices in order to generate the highest crop yields, while using fewer chemicals with lower toxicity as environmental considerations. Finally, ecological considerations have led to integrated pest management systems which further challenge the farmer's ability to produce crop yields and quality within the economic constraints prevalent in today's market.

Plant, soil and seed treatments are used on almost every commercial crop on the market today. In this era of intensified agriculture, the seed is modified to obtain higher crop yields and high quality.

As example, WO patent application WO2004071195 discloses a method to increase crop yield and accelerating crop emergence comprising administering a composition including a polysaccharide on a seed or seed piece of said crop or to a soil in which said crop is cultivated. U.S. Pat. No. 5,554,445 describes a seed encrusting method by use of microcrystalline chitosan in a form of liquid dispersion to form a highly adhesive, permeable, biodegradable and bioactive film on the seed surface. The seed encrusting preparation consists of providing a uniform coating of the seed with a mixture of seed, encrusting agent and/or dyes and/or nutrient media that the preparation is optionally combined with. However the germination power mentioned in this prior art is clearly not sufficient as the number of sprouted plants may be increased but without a significant improvement of growth.

There is a need then to carry out a method to improve the germination rate and is the crop yield but also the enhancement of growth of the obtained plant, notably permitting to develop and increase its biomass.

INVENTION

It appear that now it's possible to set a seed treatment permitting to increase the enhancement of growth of a plant, notably permitting to develop its biomass and reach its maturity; that could not be obtained by the seed treatments involved in the prior art. The seed treatment also permits to increase the number of pods, the weight of grains and size, the length of roots and the general yield of produced plants, even in conditions wherein irrigation is insufficient.

The present invention concerns then a method to increase the growth of a plant which comprises at least a step to coat a seed of said plant with a composition comprising at least one of the cationic compounds chosen in the group consisting of: homopolymers and copolymers of cationic styrenic monomers, homopolymers and copolymers of cationic allylic monomers, homopolymers and copolymers of (meth) acrylamido cationic monomers, homopolymers and copolymers of (meth)acrylate cationic monomers, polyvinylamine, cationic polyacrylamide, cationic polyvinyl alcohol, Polyquaternium-2; polyureylene ammonium salt , cationic starch, cationic cellulose, cationic hydroxyl-ethyl cellulose, cationic xanthan gum, cationic carageenan gum, cationic karaya gum, cationic arabic gum, cationic Lara gum, cationic canafen gum, cationic cassia gum, cationic konjac gum, cationic daincha, cationic fenugreek gum, cationic locust bean gum, cationic psyllium seed gum, cationic konjak, cationic mesquite gum, cationic ivory nut mannan gum, cationic alginate, cationic agar, cationic ulvane, cationic tragacanth gum, cationic ghatti gum, cationic tamarind gum, cationic xyloglucan, cationic inulin, cationic proteins, cationic pectin and cationic hemicellulose.

The invention also concerns a method to increase the growth of a plant comprising administering a composition comprising at least one of the above mentioned compounds on a seed of said plant.

It is also an object of this invention to provide a method, which is easily carried out and easily applied using conventional and commercially available application equipment.

The method of the present invention involving a cationic compound also permits to decrease the detrimental effect of fungicide and herbicides that impact negatively germination rate and growth of plants.

Other characteristics, details and advantages of the invention will emerge even. more fully upon reading the description which follows.

Throughout the description, including the claims, the term "comprising one" should be understood as being synonymous with the term "comprising at least one", unless otherwise specified, and "between" should be understood as being inclusive of the limits.

Should the disclosure of any patents, patent applications, and publications which are incorporated herein by reference conflict with the description of the present application to the extent that it may render a term unclear, the present description shall take precedence.

As used herein, "alkyl" groups include saturated hydrocarbons having one or more carbon atoms, including straight-chain alkyl groups, such as methyl, ethyl, propyl, butyl, pentyl, hexyl, heptyl, octyl, nonyl, decyl, cyclic alkyl groups (or "cycloalkyl" or "alicyclic" or "carbocyclic" groups), such as cyclopropyl, cyclopentyl, cyclohexyl, cycloheptyl, and cyclooctyl, branched-chain alkyl groups, such as isopropyl, tert-butyl, sec-butyl, and isobutyl, and alkyl-substituted alkyl groups, such as alkyl-substituted cycloalkyl groups and cycloalkyl-substituted alkyl groups. In complex structures, the chains may be branched, bridged, or cross-linked

DETAILS OF THE INVENTION

Seeds

Plants according to the present invention may be agricultural and horticultural plants, shrubs, trees and grasses, hereinafter sometimes collectively referred to as plants.

Seed is of the crop or plant species including but not limited to corn (*Zea mays*), *Brassica* sp. (e.g., *B. napus, B. rapa, B. juncea*), alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus animus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, woody plants such as conifers and deciduous trees, squash, pumpkin, hemp, zucchini, apple, pear, quince, melon, plum, cherry, peach, nectarine, apricot, strawberry, grape, raspberry, blackberry, soybean, sorghum, sugarcane, rapeseed, clover, carrot, and *Arabidopsis thaliana*.

In one embodiment, the seed is of any vegetables species including but not limited to tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), cauliflower, broccoli, turnip, radish, spinach, asparagus, onion, garlic, pepper, celery, and members of the genus Cucumis such as cucumber (*C. sativus*), cantaloupe (*C. cantalupensis*), and musk melon (*C. melo*).

In one embodiment, the seed is of any ornamentals species including but not limited to hydrangea (*Macrophylla hydrangea*), hibiscus (*Hibiscus rosasanensis*), petunias (*Petunia hybrida*), roses (*Rosa* spp.), azalea (*Rhododendron* spp.), tulips (*Tulipa* spp.), daffodils (*Narcissus* spp.), carnation (*Dianthus caryophyllus*), poinsettia (*Euphorbia pulchenima*), and chrysanthemum.

In one embodiment, the seed is of any conifer species including but not limited to conifers pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

In one embodiment, the seed is of any leguminous plant species including but not limited beans and peas. Beans include guar, locust bean, fenugreek, soybean, garden beans, cowpea, mungbean, lima bean, fava bean, lentils, chickpea, pea, moth bean, broad bean, kidney bean, lentil, dry bean, etc. Legumes include, but are not limited to, Arachis, e.g., peanuts, Vicia, e.g., crown vetch, hairy vetch, adzuki bean, mung bean, and chickpea, Lupinus, e.g., lupine, trifolium, Phaseolus, e.g., common bean and lima bean, Pisum, e.g., field bean, Melilotus, e.g., clover, Medicago, e.g., alfalfa, Lotus, e.g., trefoil, lens, e.g., lentil, and false indigo. Typical forage and turf grass for use in the methods described herein include but are not limited to alfalfa, orchard grass, tall fescue, perennial ryegrass, creeping bent grass, lucerne, birdsfoot trefoil, clover, stylosanthes species, lotononis bainessii, sainfoin and redtop. Other grass species include barley, wheat, oat, rye, orchard grass, guinea grass, sorghum or turf grass plant.

In another embodiment, the seed is selected from the following crops or vegetables: corn, wheat, sorghum, soybean, tomato, cauliflower, radish, cabbage, canola, lettuce, rye grass, grass, rice, cotton, sunflower and the like.

It is understood that the term "seed" or "seedling" is not limited to a specific or particular type of species or seed. The term "seed" or "seedling" can refer to seed from a single plant species, a mixture of seed from multiple plant species, or a seed blend from various strains within a plant species. In one embodiment, crop seeds include but are not limited to rice, corn, wheat, barley, oats, soybean, cotton, sunflower, alfalfa, sorghum, rapeseed, sugarbeet, tomato, bean, carrot, tobacco or flower seeds.

Coating

The composition of the present invention may comprise one or more compounds chosen in the group consisting of: homopolymers and copolymers of cationic styrenic monomers, homopolymers and copolymers of cationic allylic monomers, homopolymers and copolymers of (meth)aciylamido cationic is monomers, homopolymers and copolymers of (meth)acrylate cationic monomers, polyvinylamine, cationic polyacrylamide, cationic polyvinyl alcohol, Polyquaternium-2; polyureylene ammonium salt , cationic starch, cationic cellulose, cationic hydroxyl-ethyl cellulose, cationic xanthan gum, cationic carageenan gum, cationic karaya gum, cationic arabic gum, cationic tara gum, cationic canafen gum, cationic cassia gum, cationic konjac gum, cationic daincha, cationic fenugreek gum, cationic locust bean gum, cationic psyllium seed gum, cationic konjak, cationic mesquite gum, cationic ivory nut mannan gum, cationic alginate, cationic agar, cationic ulvane, cationic tragacanth gum, cationic ghatti gum, cationic tamarind gum, cationic xyloglucan, cationic inulin, cationic proteins, cationic pectin and cationic hemicellulose.

These compounds are preferably chosen in the group consisting of: cationic cassia gum, cationic fenugreek gum, cationic tara gum, cationic starch, cationic cellulose, cationic konjac gum, cationic locust bean gum, cationic tamarind gum, and cationic psyllium gum.

The present invention also concerns then a seed coated by at least a cationic compound chosen in the group consisting of: cationic cassia gum, cationic fenugreek gum, cationic tara gum, cationic starch, cationic cellulose, cationic konjac gum, cationic locust bean gum, cationic tamarind gum, and cationic psyllium gum.

Cationic compound are preferably cationic galactomannan, notably chosen in the group consisting of : cationic fenugreek gum, cationic tara gum, cationic locust bean gum, and cationic cassia gum.

The present invention also concerns then a seed coated by at least a cationic is galactomannan, notably chosen in the group consisting of cationic fenugreek gum, cationic tara gum, cationic locust bean gum and cationic cassia gum.

Cassia gum is usually a food additive made from the endosperm of Senna obtusifolia (also called Cassia obtusifolia or Cassia tora). It is used as a thickener and gelling agent, and has E-number E427. Cassia gum may also be a Cassia angustifolia seed gum, known to be an effective natural coagulant for decolourisation of dye solutions. Cassia gum is mainly constituted of galactomanna with a mannose:galactose number ratio is about 5:1.

Fenugreek gum is a galactomannan extracted for the seeds of the fenugreek plant, Trigonella Foenum-Gracecum, Fenugreek gum is a non gelling hydrocolloid, which is soluble in cold water. Galactomannans are polysaccharides consisting of a mannose backbone with galactose side groups (more specifically, a (1-4)-linked beta-D-mannopyranose backbone with branchpoints from their 6-positions linked to alpha-D-galactose, i.e. 1-6-linked alpha-D-galactopyranose). In fenugreek gum, mannose:galactose number ratio is about 1:1. Canafen® and Coyote ® are known brands of fenukreek gums.

Tara gum is a natural additive, obtained by grinding the endosperm of the seeds of Caesalpinia spinosa, of the Leguminosae family. Tara gum, also called Peruvian carob. Tara gum is mainly constituted of galactomannans with a mannose:galactose number ratio is about 3:1. Tara gum is also known with the following CAS reference: CAS No.39300-88-4.

Starch or amylum is a carbohydrate consisting of a large number of glucose units joined by glycosidic bonds. Cationic starch may be produced according to U.S. Pat. No. 4,464,528.

Cellulose is an organic compound with the formula $(C_6H_{10}O_5)_n$, polysaccharide consisting of a linear chain of several hundred to over ten thousand β (1→4) linked D-glucose units.

Konjac gum is obtained from Amorphophallus Konjac and mainly comprises glucomannan, known to be a food additive used as an emulsifier and thickener. Glucomannan is mainly a straight-chain polymer, with a small amount of branching The component sugars are β-(1→4)-linked D-mannose and D-glucose in a ratio of 1.6:1.

Locust bean gum is a galactomannan vegetable gum extracted from the seeds of the carob tree, mostly found in the Mediterranean region. Locust bean gum is mainly constituted of galactomannans with a mannose:galactose number ratio is about 4:1. Locust bean gum is also known with the following CAS reference: CAS No. 9000-40-2.

Cationic compound of the invention may include compounds that may be obtained by the use of different possible cationic etherifying agents, such as for example the family of ammonium salts, notably quaternary ammonium salts, phosphonium salts and sulfonium salts.

In the case of cationic compounds, the cationic group may be then an amine group (primary, secondary or tertiary) or a quaternary ammonium group bearing four radicals, which may be identical or different, chosen an alkyl radical containing from 1 to 22 carbon atoms, more particularly from 1 to 14 and advantageously from 1 to 3 carbon atoms. The counterion is generally a halogen, which is one embodiment is chlorine, or nitrate.

Suitable quaternary ammonium compounds may be those conforming to the general Formula (I):

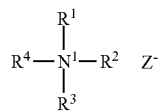

wherein where $R^1$, $R^2$ and $R^3$ are methyl or ethyl groups; $R^4$ is either an epoxyalkyl group of the general Formula (II):

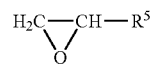

or $R^4$ is a halohydrin group of the general Formula

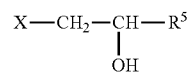

wherein $R^3$ is a $C_1$ to $C_3$ alkylene; X is chlorine or bromine, and Z is an anion such as Cl, Br, I or $HSO_4$.

Quaternary ammonium salts may be for example : 3-chloro-2-hydroxypropyl trimethyl ammonium chloride (CHPTMAC), 2,3-epoxypropyl trimethyl ammonium chloride (EPTAC), and diallyldimethyl ammonium chloride (DMDAAC).

A typical cationic functional group in these cationic compounds is trimethylamino(2-hydroxyl)propyl, with a counter ion. Various counter ions can be utilized, including but not limited to halides, such as chloride, fluoride, bromide, and iodide, sulfate, methylsulfate, nitrate, and mixtures thereof Cationic compounds of the present invention may be chosen in the group consisting of:
- homopolymers and copolymers of cationic styrenic monomers, such as vinylbenzyl trimethyl ammonium chloride,
- homopolymers and copolymers of cationic allylic monomers, such as diallyldimethyl ammonium chloride, and poly DMDAAC,
- homopolymers and copolymers of (meth)acrylamido cationic monomers, such as acrylamidopropyltrimonium chloride, and polyMAPTAC,
- homopolymers and copolymers of (meth)acrylate cationic monomers, such as trimethylammonium ethyl acrylate, polyADAME quat or trimethylammonium ethyl methacrylate, and poly MADAME quat, Cationic compounds of the present invention may be preferably chosen in the group consisting of: 2,3-hydroxypropyl trimethyl ammonium chloride, vinylbenzyl trimethyl ammonium chloride, diallyidimethyl ammonium chloride, acrylamidopropyltrimonium chloride, trimethylammonium ethyl (meth) acrylate chloride.

The degree of hydroxyalkylation (molar substitution or MS) of cationic compounds, that is the number of alkylene oxide molecules consumed by the number of free hydroxyl functions present on the compounds, may be comprised between 0 and 3, preferably between 0 and 1.7. As example, a MS of 1. may represent one propylene oxide unit per repeating monomer unit.

The Degree of Substitution (DS) of cationic compounds, that is the average number of hydroxyl groups that have been substituted by a cationic group per monosaccharide unit, may be comprised between 0.005 and 3, preferably between 0.01 and 2, more preferably between 0.05 and 0.15. DS may notably represent the number of the cationic groups per repeated monomer unit. DS may notably be determined by titration.

The Charge Density (CD) of cationic compounds may be comprised between is 0.1 and 10 meq/g, preferably between 0.4 and 6 meq/g. The charge density refers to the ratio of the number of positive charges on a monomeric unit of which a polymer is comprised to the molecular weight of said monomeric unit. The charge density multiplied by the polymer molecular weight determines the number of positively charged sites on a given polymer chain.

Specific cationic compounds may have an average Molecular Weight (Mw) of between about 20,000 daltons and 20,000,000 daltons. This notably the case for cationic compounds such as poly diallyldimethyl ammonium chloride (poly DMDAAC), polymethacrylamidopropyltrimonium chloride, polyMAPTAC, Polyquatemium-2, and polyureylene ammonium salt.

The cationic compounds may also have an average Molecular Weight (Mw) of between about 100,000 daltons and 3,500,000 daltons, preferably between about 500,000 daltons and 3,500,000 daltons.

The seed coating composition may also comprise a binder. The binder (or any of the layers) can be molasses, granulated sugar, alginates, karaya gum, jaguar gum, tragacanth gum, polysaccharide gum, mucilage, gelatin, polyvinyl acetates, polyvinyl acetate copolymers, polyvinyl alcohols, polyvinyl alcohol copolymers, styrene acrylate polymers, styrene butadiene polymers, polyurethanes, celluloses (including ethylcelluloses and methylcelluloses, hydroxypropylcelluloses, hydroxymethyl celluloses, hydroxymethylpropyl-celluloses), polyvinylpyrolidones, dextrins, malto-dextrins, polysaccharides, fats, oils, proteins, gum arabics, shellacs, vinylidene chloride, vinylidene chloride copolymers, calcium lignosulfonates, acrylic copolymers, starches, derivatized starches, polyvinylacrylates, zeins, carboxymethylcellulose, chitosan, polyethylene oxide, acrylimide polymers and copolymers, polyhydroxyethyl acrylate, methylacrylimide monomers, alginate, ethylcellulose, polychloroprene, syrups or any combination thereof.

The seed coating composition may contain also surfactants, antioxidants, plasticizers, colorants, fillers, drying powder type silica (including fumed or precipitated silica), kaolin, talc, or a mixture thereof.

In another embodiment, the seed coating composition contains at least one active ingredient. The active ingredient can be one or more herbicides, plant growth regulators, crop dessicants, fungicides, bacteriocides, bacteriostats, insecticides, insect repellants, triazine herbicides, sulfonylurea herbicides, uracils, urea herbicides, acetanilide herbicides, organophosphonate herbicides, glyphosate salts, glyphosate esters, nitrilo oxime fungicides, imidazole fungicides, triazole fungicides, sulfenamide fungicides, dithio-carbamate fungicides, chloronated aromatic, dichloro aniline fungicides, carbamate insecticides, organo thiophosphate insecticides; perchlorinated organic insecticides, methoxychlor, miticides, propynyl sulfite, triazapentadiene miticides, chlorinated aromatic miticides, tetradifan, dinitrophenol miticides, binapacryl, molluscicides, bactericides, repellents or any mixture thereof.

The seed coating composition may contain also nutrients, fertilizers or biological additives, such as inoculants type bacteria or fungi, including mycorrhizal, or a mixture thereof.

According to an embodiment of the present invention, the seeding composition comprises at least a cationic compounds and a plant biostimulant. Plant biostimulants are usually components other than fertilizers that affect plant growth and/or metabolism upon foliar application or when added to soil. Plant biostimulants generally fall within one of three categories: hormone-containing products, amino acid-containing products and humic acid-containing products. Plant biostimulants are used to treat crops in a commercial setting in view of their ability to, for example, increase growth rates, decrease pest plant growth, increase stress tolerance, increase photosynthetic rate, and increase disease tolerance. Plant biostimulants are generally believed to operate by up-regulating or down-regulating plant hormones.

The seed coating composition may also contain pigments, adjuvants, surfactants, and/or fertilizers.

The seed coating composition may be a liquid or solid composition, notably a powder. Suitable coating techniques may be utilized to coat the seeds or agglomeration of seed of the seed coating compositions described herein. Equipment that may be utilized for coating can include but are not limited to drum coaters, rotary coaters, tumbling drums, fluidized beds and spouted beds, but any suitable equipment or technique may be employed. The seeds may be coated via a batch or continuous coating process.

Process

In a first embodiment, the invention also concerns a method to increase the growth of a plant by coating a seed of said plant with a composition comprising at least one of the above mentioned compounds in a first step and then in a second step to apply the coated seed onto or in the soil; notably in order to set in contact the coated seed with the ground.

In an other embodiment, the invention also concerns a method to increase the growth of a plant in which it's perfectly possible to set an "in situ coating" onto or in the soil; notably by implanting in a hole in the soil a raw or non-coated seed of plant and then applying a coating composition comprising at least one of the above mentioned compounds, into the hole to surround or partially surround the seed.

The invention also concerns then a method to increase the growth of a plant comprising administering a composition comprising at least one of the above mentioned compounds to a soil in which said crop is cultivated.

The seeds can be separated prior to coating which, in one embodiment, utilizes mechanical means such as a sieve. The separated seeds can then be introduced into a coating machine having a seed reservoir. in one embodiment, the seeds in the mixing bowl are combined with one or more of the coatings described herein and adhered with a binder or adhesive.

In one embodiment of the process, one or more layers can be added to coat the seed or agglomeration. Outer layers can be introduced sequentially to the rotating drum.

In another embodiment, agglomerators or agglomerator devices may also be utilized. Coating is performed within a rotary coater by placing seeds within a rotating chamber, which pushes the seeds against the inside wail of the chamber. Centrifugal forces and mixing bars placed inside the coater allow the seed to rotate and mix with a coating layer. Binder or other coating materials can be pumped into the proximate center of the coater onto an atomizer disk that rotates along with the coating chamber. Upon hitting the atomizer disk, liquid adhesive is then directed outward in small drops onto the seed.

In one embodiment, seed coating techniques include, for example, seed in a is rotating pan or drum. Seed is then mist with water or other liquid and then gradually a fine inert powder, e.g., diatomaceous earth, is added to the coating pan. Each misted seed becomes the center of a mass of powder, layers, or coatings that gradually increases in size. The mass is then rounded and smoothed by the tumbling action in the pan, similar to pebbles on the beach. The coating layers are compacted by compression from the weight of material in the pan. Binders often are incorporated near the end of the coating process to harden the outer layer of the mass. Binders can also reduce the amount of dust produced by the finished product in handling, shipping and sowing. Screening techniques, such as frequent hand screening, are often times utilized to eliminate blanks or doubles, and to ensure uniform size. For example, tolerance for seed coating compositions described herein can be +/−1/64th inch (0.4 mm), which is the US seed trade standard for sizing, established long before coatings were introduced. For example, coated lettuce seed is sown most frequently with a belt planter through a 13/64inch diameter round holes in the belt. This hole size requires that the seed coating compositions comprising lettuce seeds can be sized over a 7.5/64inch screen and through an 8.5/64inch screen.

In another embodiment, the seed coating compositions and methods described herein comprises "in situ coating". In situ coating means, in one embodiment, where a raw or non-coated seed is implanted in a hole in the ground and Immediately or soon thereafter a coating composition i sprayed or applied directly into the hole to surround or partially surround the seed. According to the invention the hole may notably be a hole, a cavity or a hollowed area, Typically, the application of the seed as well as application of the ,coating composition are performed mechanically, but is understood that either or both of the referenced applications can be performed manually as well.

The following examples are included to illustrate embodiments of the invention, Needless to say, the invention is not limited to described examples.

EXPERIMENTAL PART

In these experiments, cationic based additives are used accordingly

| | ADDITIVE | DS | Mw |
|---|---|---|---|
| 2 | Cationic cassia gum from *Angustifolia* leaves | 0.10 | 1M |
| 3 | Cationic fenugreek gum (canafen gum) | 0.12 | $2.59 \times 10^6$ |
| 4 | Cationic konjac gum | 0.14 | $1.09 \times 10^6$ |
| 5 | Cationic tara gum | 0.12 | $1.71 \times 10^6$ |

Production of Cationic Fenugreek, Cationic Konjac and Cationic Tara:

In a 1 liter stirred reactor, 327 g of isopropanol solvent mixed with 140 g of de-ionized water are introduced at room temperature, under a blanket of inert nitrogen gas. 100 g of polysaccharide flour are then loaded at room temperature and under vigorous stirring. After a few minutes of stirring to allow for homogenization 22 g of 2,3-epoxypropyltrimethylammonium chloride are added. This reagent is left to mix at room temperature with the guar dispersion for 20 minutes, after which 10 g of sodium hydroxide 25%, are added slowly. The dispersion is then heated. to 65° C. and held at this temperature for 90 minutes, after which the temperature is lowered to at least 50° C. in order to start the washing procedure.

A reaction mixture obtained as described in the paragraph above is dispersed under stirring with 178 g of isopropanol, 45 g of water and 3-4 g of acetic acid. It is then left under stirring for 15 minutes and then discharged from the reactor. This dispersion is then filtered under vacuum through qualitative paper filter. This washing and filtering procedure is repeated once more for a 30 minute interval with 240 g of isopropanol mixed with 60 g of water. The obtained guar powder is finally mixed with 300g of isopropanol, left to stir for 30 minutes, and filtered: The collected solids were then left to dry overnight in air and then for 4 h in a vacuum oven at 50° C.

The analytical results obtained for the above samples are shown in the above table: it contains $DS_{cationic}$ by 1H NMR after acidic extraction, and molecular weight determined by SEC-LS.

Production of Cationic Cassia Gum from Angustifolia Leaves:

Cationic cassia gum is produced according to the process described by WO2004/112733 application by reaction with glycidyltrimethylammonium chloride.

Example 1

Growth Enhancement On Wheat Seeds

Spraying with 0.4 wt % of aqueous solution of additives on the surface of Wheat seeds, to obtain a weight ratio additive/seed of 0.2%. The germination test is carried out on wet paper surface in a climate chamber and germination box was covered. so no more water was needed during the test, with a temperature of 15° C. or 25° C. Root length after several days is hence calculated for 20 seeds. DAP is day after planting.

| Additive | Root length after 7 DAP (mm) 15° C. | Root length after 4 DAP (mm) 25° C. |
|---|---|---|
| None. Control | 60.0 | 76.0 |
| 1 | 68.2 | 83.0 |
| 2 | 67.8 | 92.0 |
| 3 | 67.7 | 95.0 |
| 4 | 68.2 | nm |
| 5 | 61.1 | 85.0 |

Example 2

Growth Enhancement On Cabbage

Spraying with 1 wt % of aqueous solution of additives on the surface of *Brassica chinensis* seed (Chinese Cabbage), to obtain a weight ratio additive/seed of 0.5%. 50 g of sand in each pot are used; this sand coming from ShanXi province. The germination test is carried out in a climate chamber under watering conditions of initial soil humidity being 38 wt % (water/soil wt %) followed by no more irrigation, with a temperature is 25° C. Germination number is then calculated for 40 pots (5 seeds by pot).

| Additive | Germination number (86 h) |
|---|---|
| None. Control | 159 |
| 1 | 171 |
| 2 | 172 |
| 3 | 163 |
| 4 | 164 |

It appears then that the seed treatment of the present invention permits to increase the germination rate but also to boost the germination early in comparison with seeds that do not provide a coating treatment.

What is claimed is:

1. A method to increase the growth of a plant, comprising coating a seed of said plant with a composition comprising at least one cationic compound selected from the group consisting of homopolymers and copolymers of cationic styrenic monomers, homopolymers and copolymers of cationic allylic monomers, homopolymers and copolymers of (meth)acrylamido cationic monomers, homopolymers and copolymers of (meth)acrylate cationic monomers, polyvinylamine, cationic polyacrylamide, cationic polyvinyl alcohol, Polyquaternium-2, polyureylene ammonium salt, cationic starch, cationic cellulose, cationic hydroxyl-ethyl cellulose, cationic xanthan gum, cationic carageenan gum, cationic karaya gum, cationic arabic gum, cationic tara gum, cationic canafen gum, cationic cassia gum, cationic konjac gum, cationic daincha, cationic fenugreek gum, cationic locust bean gum, cationic psyllium seed gum, cationic konjak, cationic mesquite gum, cationic ivory nut mannan gum, cationic alginate, cationic agar, cationic ulvane, cationic tragacanth gum, cationic ghatti gum, cationic tamarind gum, cationic xyloglucan, cationic inulin, cationic proteins, cationic pectin, and cationic hemicellulose, wherein the at least one cationic compound has an average Molecular Weight of from about 20,000 Daltons to 20,000,000 Daltons.

2. The method according to claim 1, wherein the at least one cationic compound is selected from the group consisting of cationic cassia gum, cationic fenugreek gum, cationic tara gum, cationic starch, cationic cellulose, cationic konjac gum, cationic locust bean gum, cationic tamarind gum, and cationic psyllium gum.

3. The method according to claim 1, wherein the at least one cationic compound comprises a cationic galactomannan selected from the group consisting of cationic fenugreek gum, cationic tara gum, and cationic locust bean gum.

4. The method according to claim 1, comprising:
a) coating a seed of plant with a composition comprising the at least one cationic compound; and
b) applying the coated seed onto or in soil.

5. The method according to claim 1, wherein the step of coating a seed comprises:
a) implanting a raw or non-coated seed in a hole in soil; and
b) applying a coating composition comprising the at least one cationic compound into the hole to surround or partially surround the seed.

6. The method according to claim 1, wherein the seed is a seed of a plant selected from the group constituting of corn, wheat, sorghum, soybean, tomato, cauliflower, radish, cabbage, canola, lettuce, rye grass, grass, rice, cotton, and sunflower.

7. The method according to claim 1, wherein the at least one cationic compound is obtained with the use of a cationic etherifying agent.

8. The method according to claim 1, wherein the cationic etherifying agent is selected from the group consisting of ammonium salts, phosphonium salts, and sulfonium salts.

9. The method according to claim 8, wherein ammonium salts are selected from the group consisting of 3-chloro-2-hydroxypropyl trimethyl ammonium chloride, 2,3-epoxypropyl trimethyl ammonium chloride, and diallyldimethyl ammonium chloride.

10. The method according to claim 1, wherein the at least one cationic compound is selected from the group consisting of:
homopolymers and copolymers of cationic styrenic monomers,
homopolymers and copolymers of cationic allylic monomers,
homopolymers and copolymers of (meth)acrylamido cationic monomers, and
homopolymers and copolymers of (meth)acrylate cationic monomers.

11. The method according to claim 1, wherein the at least one cationic compound is selected from the group consisting of 2,3-hydroxypropyl trimethyl ammonium chloride, vinylbenzyl trimethyl ammonium chloride, diallyldimethyl ammonium chloride, acrylamidopropyltrimonium chloride, and trimethylammonium ethyl (meth) acrylate chloride.

12. The method according to claim 2, wherein the at least one cationic compound has a Degree of Substitution of cationic compounds of from 0.005 to 3.

13. The method according to claim 2, wherein the at least one cationic compound has a Degree of Substitution of cationic compounds of from 0.01 to 2.

14. The method according to claim 1, wherein the composition further comprises a binder.

15. The method according to claim 1, wherein the composition further comprises an active ingredient.

16. The method according to claim 1, wherein the composition further comprises a plant biostimulant.

17. A seed coated by at least one cationic compound selected from the group consisting of cationic cassia gum, cationic fenugreek gum, cationic tara gum, cationic starch, cationic cellulose, cationic konjac gum, cationic locust bean gum, cationic tamarind gum, and cationic psyllium gum, wherein the at least one cationic compound has an average Molecular Weight of from about 20,000 Daltons to 20,000,000 Daltons.

18. A seed coated by at least one cationic galactomannan selected from the group consisting of: cationic fenugreek gum, cationic tara gum, cationic locust bean gum, and cationic cassia gum, wherein the at least one cationic compound has an average Molecular Weight of from about 20,000 Daltons to 20,000,000 Daltons.

* * * * *